US009555151B2

(12) United States Patent
Taylor et al.

(10) Patent No.: US 9,555,151 B2
(45) Date of Patent: Jan. 31, 2017

(54) SYSTEMS AND METHODS FOR INCONTINENCE CONTROL

(71) Applicant: SOFT HEALTH TECHNOLOGIES LLC, Aliso Viejo, CA (US)

(72) Inventors: John M. Taylor, Trabuco Canyon, CA (US); Thomas J. Berryman, Laguna Beach, CA (US)

(73) Assignee: SOFT HEALTH TECHNOLOGIES, LLC, Aliso Viejo, CA (US)

( * ) Notice: Subject to any disclaimer, the term of this patent is extended or adjusted under 35 U.S.C. 154(b) by 44 days.

(21) Appl. No.: 14/870,136

(22) Filed: Sep. 30, 2015

(65) Prior Publication Data

US 2016/0095759 A1     Apr. 7, 2016

Related U.S. Application Data

(60) Provisional application No. 62/059,833, filed on Oct. 3, 2014.

(51) Int. Cl.
*A61F 13/472*     (2006.01)
*A61L 15/28*      (2006.01)
(Continued)

(52) U.S. Cl.
CPC .............. *A61L 15/46* (2013.01); *A61F 2/005* (2013.01); *A61F 2/0009* (2013.01); *A61F 13/00063* (2013.01); *A61F 13/47209* (2013.01); *A61F 13/47227* (2013.01); *A61L 15/18* (2013.01); *A61L 15/20* (2013.01); *A61L 15/26* (2013.01); *A61L 15/28* (2013.01); *A61L 15/40* (2013.01); *A61L 15/425* (2013.01); *A61L 15/58* (2013.01); *A61F 2013/15121* (2013.01); *A61F 2210/00* (2013.01); *A61F 2220/0008* (2013.01);
(Continued)

(58) Field of Classification Search
CPC combination set(s) only.
See application file for complete search history.

(56) References Cited

U.S. PATENT DOCUMENTS 4,593,053 A    6/1986  Jevne et al.
5,074,855 A   12/1991  Rosenbluth et al.
(Continued)

FOREIGN PATENT DOCUMENTS

JP    2005-065750 A    3/2005
JP    2005-160845 A    6/2005

OTHER PUBLICATIONS

PCT International Search Report and Written Opinion for PCT/US2015/053367, Applicant: Soft Health Technologies, LLC, Forms PCT/ISA/220, 210, and 237 dated Feb. 4, 2016 (14 pages).
(Continued)

*Primary Examiner* — Tatyana Zalukaeva
*Assistant Examiner* — Guy K Townsend
(74) *Attorney, Agent, or Firm* — Blair Walker IP Services, LLC

(57) ABSTRACT

A system for managing female incontinence includes a body of biocompatible material configured to fit between the labia minora and the vestibule floor, the body having a surface configured to occlude the urethral meatus, an adhesive carried on at least a first portion of the surface and configured to provide a sealing engagement between the body and the urethral meatus, and wherein at least the adhesive includes a water gradient silicone hydrogel.

30 Claims, 5 Drawing Sheets

(51) Int. Cl.
| | |
|---|---|
| A61L 15/58 | (2006.01) |
| A61L 15/18 | (2006.01) |
| A61L 15/46 | (2006.01) |
| A61F 2/00 | (2006.01) |
| A61F 13/00 | (2006.01) |
| A61L 15/20 | (2006.01) |
| A61L 15/26 | (2006.01) |
| A61L 15/40 | (2006.01) |
| A61L 15/42 | (2006.01) |
| A61F 13/15 | (2006.01) |

(52) U.S. Cl.
CPC ......... *A61F 2230/0063* (2013.01); *A61F 2250/0067* (2013.01); *A61F 2250/0078* (2013.01); *A61F 2310/00389* (2013.01); *A61L 2300/102* (2013.01); *A61L 2300/108* (2013.01); *A61L 2300/216* (2013.01); *A61L 2300/30* (2013.01); *A61L 2300/606* (2013.01)

(56) References Cited

U.S. PATENT DOCUMENTS

| | | | |
|---|---|---|---|
| 5,171,302 A * | 12/1992 | Buell | A61F 13/47227 604/358 |
| 5,197,959 A * | 3/1993 | Buell | A61F 13/15203 604/358 |
| 5,270,358 A * | 12/1993 | Asmus | A61L 24/043 424/448 |
| 5,336,208 A | 8/1994 | Rosenbluth et al. | |
| 5,508,317 A | 4/1996 | Müller | |
| 5,769,091 A | 6/1998 | Simon et al. | |
| 5,885,265 A * | 3/1999 | Osborn, III | A61F 13/15211 604/367 |
| 5,927,282 A | 7/1999 | Lenker et al. | |
| 6,131,575 A | 10/2000 | Lenker et al. | |
| 6,355,022 B1 | 3/2002 | Osborn, III et al. | |
| 6,432,096 B1 * | 8/2002 | McFall | A61F 13/47209 604/385.17 |
| 6,461,340 B1 | 10/2002 | Lenker et al. | |
| 6,613,955 B1 * | 9/2003 | Lindsay | A61F 13/4704 604/378 |
| 6,800,225 B1 | 10/2004 | Hagmann et al. | |
| 8,163,206 B2 | 4/2012 | Chang et al. | |
| 9,408,684 B2 * | 8/2016 | Berryman | A61F 2/0009 |
| 2001/0021833 A1 | 9/2001 | Schmidt et al. | |
| 2001/0026810 A1 * | 10/2001 | McGhee | A61K 45/06 424/486 |
| 2003/0100877 A1 | 5/2003 | Erdman | |
| 2003/0191442 A1 * | 10/2003 | Bewick-Sonntag | A61F 13/47209 604/385.17 |
| 2004/0266302 A1 | 12/2004 | DiSalvo et al. | |
| 2009/0182296 A1 | 7/2009 | Dennis et al. | |
| 2009/0221980 A1 | 9/2009 | Mosbacher et al. | |
| 2010/0198177 A1 * | 8/2010 | Yahiaoui | A61F 13/82 604/359 |
| 2011/0008277 A1 * | 1/2011 | Bruggeman | A61L 27/16 424/78.37 |
| 2011/0086077 A1 | 4/2011 | McCrea et al. | |
| 2012/0026458 A1 | 2/2012 | Qiu et al. | |
| 2015/0094393 A1 | 4/2015 | Holland et al. | |

OTHER PUBLICATIONS

Brubaker, L., Harris, T., Gleason, D., Newman, D., North, B., Miniguard Investigation Group, "The External Urethral Barrier for Stress Incontinence: a Multicenter Trial of Safety and Efficacy", Obstetrics & Gynecology, Jun. 1999, pp. 932-937, vol. 93, No. 6, Elsevier, New York, USA.

Toumanides, S., Sideris, E., Agricola, T., Moulopoulos, S., "Transcatheter Patch Occlusion of the Left Atrial Appendage Using Surgical Adhesives in High-Risk Patients with Atrial Fibrillation", Journal of the American College of Cardiology, Nov. 15, 2011, pp. 2236-2240, vol. 58, No. 21, Elsevier, New York, USA.

Weeks, A., Morrison, D., Alauzun, J., Brook, M., Jones, L., Sheardown, H., "Photocrosslinkable hyaluronic acid as an internal wetting agent in model conventional and silicone hydrogel contact lenses", Journal of Biomedical Materials Research A, Aug. 2012, pp. 1972-1982, vol. 100A, No. 8, John Wiley & Sons, Hoboken, USA.

Patent No. JP 2005-065750A, Shinohara et al., published Mar. 17, 2005. English translation of paragraphs [0004], [0049], [0055], [0132], [0133], [0134], [0141], [0146], [0147], [0148], [0149], [0150], [0151], [0153], [0156], [0157], [0180], [0188], [0189], [0202], [0203], [0227], [0228], [0229], [0230], [0231], [0232].

Jones, L., Tighe B. "Silicone Hydrogel Contact Lens Materials Update—Part 1", Printed from Internet May 2, 2016, pp. 1-4, URL http://siliconehydrogels.org/editorials/index_july.asp.

Jones, L., Tighe, B., "Silicone Hydrogel Contact Lens Materials Update—Part 2", Printed from Internet May 2, 2016, pp. 1-4, URL http://siliconehydrogels.org/editorials/index_august.asp.

Zhao, Z., Xie, H., An, S., Jiang, Y., "The Relationship between Oxygen Permeability and Phase Separation Morphology in the Multicomponent Silicone Hydrogels", The Journal of Physical Chemistry B, Dec. 2014, pp. 14640-14647, vol. 118, No. 50, American Chemical Society, Washington D.C., USA.

* cited by examiner

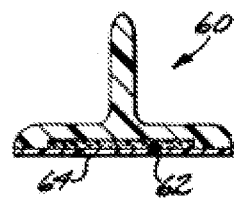
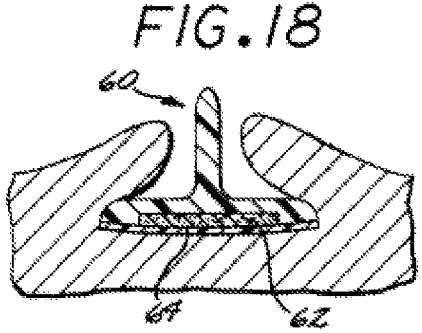
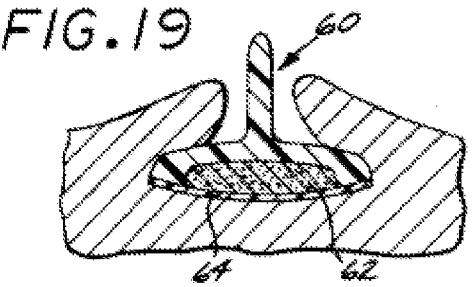
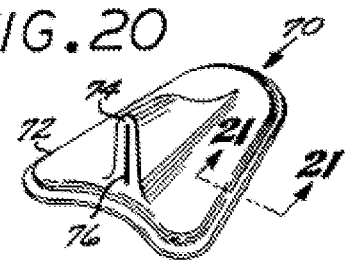
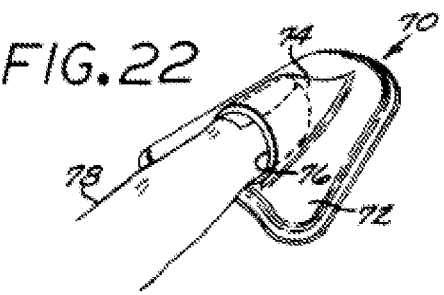
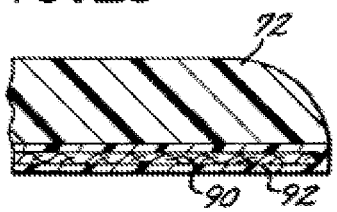
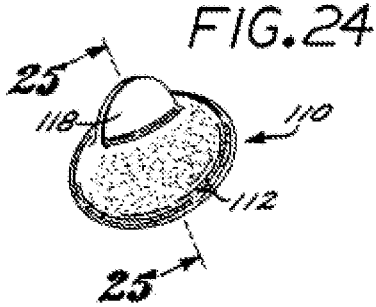
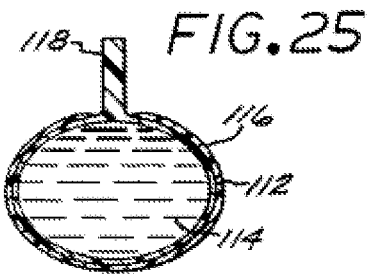

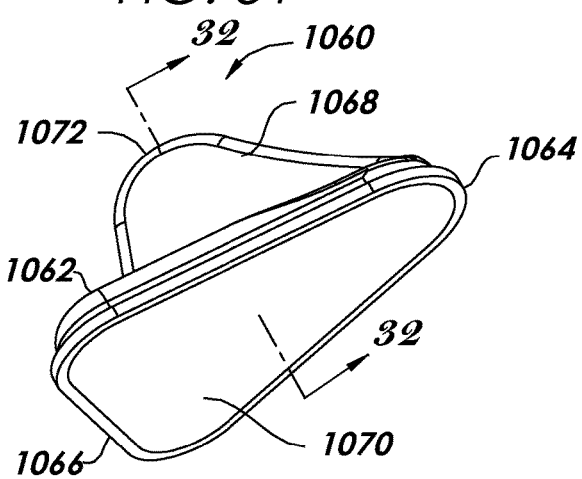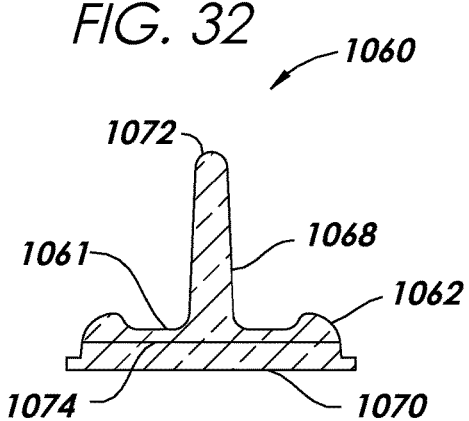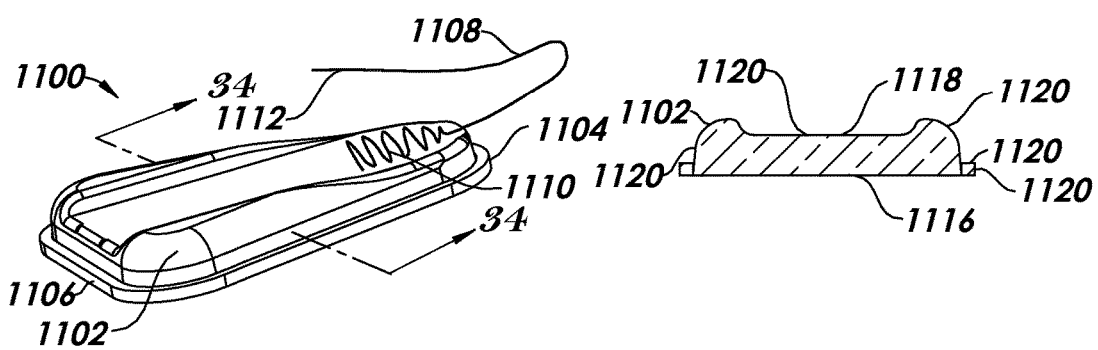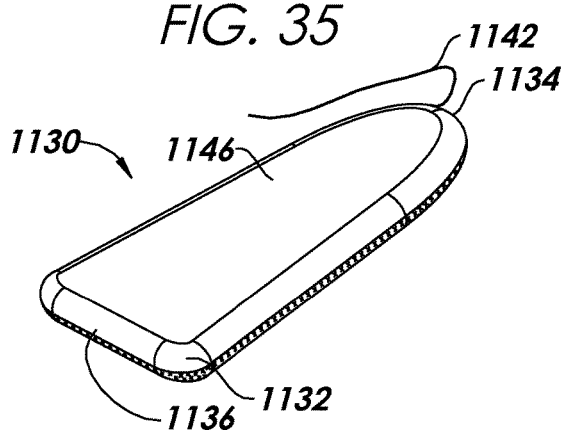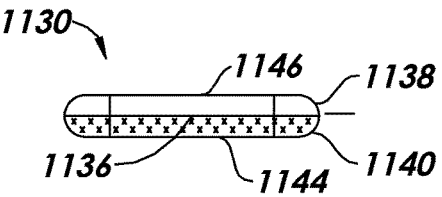

SYSTEMS AND METHODS FOR INCONTINENCE CONTROL

INCORPORATION BY REFERENCE TO ANY PRIORITY APPLICATIONS

This application claims the benefit of priority to U.S. Provisional Application No. 62/059,833, filed on Oct. 3, 2014, which is incorporated in its entirety by reference herein for all purposes. Priority is claimed pursuant to 35 U.S.C. §119.

FIELD OF THE INVENTION

The field of the invention generally relates to devices for treating urinary incontinence.

BACKGROUND

Urinary incontinence is a troublesome problem for many individuals. Urinary stress incontinence is a particular form of urinary incontinence wherein a physical occurrence may cause unwanted leakage of urine. For example, a sudden spike in abdominal pressure from sneezing, coughing or exercise may exceed the resistive pressure of the urethra for a brief moment, causing an involuntary leakage of urine. Stress urinary incontinence occurs predominantly in adult women, but may also occur in certain male or in younger females.

Absorbent pads are available which absorb urine after it has leaked and contain it within the wearer's undergarments. Adult diapers or absorbent panties or underwear may also be used to absorb the urine. Plastic pants designed to fit over undergarments are another means of protecting outer clothing for urine which has leaked. All of these products have the disadvantage of being forced to contain the wetness and odor of leaked urine.

More recently, urinary incontinence pads which are adhesively applied directly over the urethral meatus have been used in women with the intent of more completely sealing the urethra, and preventing the involuntary leakage of urine.

SUMMARY OF THE INVENTION

In a first embodiment of the invention, a system for managing female incontinence includes a body of biocompatible material configured to fit between the labia minora and the vestibule floor, the body having a surface configured to occlude the urethral meatus, an adhesive carried on at least a first portion of the surface and configured to provide a sealing engagement between the body and the urethral meatus, and wherein at least the adhesive includes a water gradient silicone hydrogel.

BRIEF DESCRIPTION OF THE DRAWINGS

FIG. 17 is a cross-sectional view of a fourth modification of the first embodiment, wherein the female urinary incontinence device includes a layer of super-absorbent material.
FIG. 18 is a cross-sectional view, similar to that of FIG. 17, showing the female urinary incontinence device as installed in the external genitalia of a human female.
FIG. 19 is a cross-sectional view, similar to that of FIG. 18, showing the super-absorbent material after it has absorbed moisture.
FIG. 20 is a perspective view of a fifth modified form of the first embodiment, which includes a finger hole.
FIG. 21 is a cross-sectional view, taken along Line 21-21 of FIG. 20.
FIG. 22 is a perspective view, similar to that of FIG. 20, showing the female urinary incontinence device with a human finger inserted into the finger hole.
FIG. 23 is a cross-sectional view, similar to that of FIG. 21, showing a sixth modification of the first embodiment.
FIG. 24 is a perspective view of a third embodiment.
FIG. 25 is a cross-sectional view taken along Line 25-25 of FIG. 24.
FIG. 31 is a perspective view of an embodiment of a female urinary incontinence device.
FIG. 32 is a cross-sectional view of the female urinary incontinence device of FIG. 31 taken along line 32-32 of FIG. 31.
FIG. 33 is a perspective view of an embodiment of a female urinary incontinence device.
FIG. 34 is a cross-sectional view of the female urinary incontinence device of FIG. 33 taken along line 34-34 of FIG. 33.
FIG. 35 is a perspective view of an embodiment of a female urinary incontinence device.

FIG. 36 is a posterior elevation view of the female urinary incontinence device of FIG. 35.

DETAILED DESCRIPTION

Referring first to FIGS. 1 through 4 of the drawings, a female urinary incontinence device 10, in accordance with a first embodiment, is shown. The device comprises a body 12, formed of a resilient foam material that is biocompatible. One suitable class of materials is that of foams formed from the water actuation of prepolymers based on either toluene diisocyanate (TDI) or methylene diphenyl diisocyanate (MDI). Such prepolymers are marketed by the Dow Chemical Company, Midland, Mich., under the trademarks "HYPOL" (TDI), "HYPOL PLUS" (MDI) and "HYPOL 2002" (TDI and MDI).

Alternatively, the body 12 can be made of a biodegradable material, such as a cellulose or cotton fiber. A polyurethane foam can also be used, being rendered biodegradable by hydrolysis of a weak backbone link, such as an amine group. Other foam materials, such as polyolefins, can be used and made hydrolytically biodegradable by using weak links such as starches in the polymer backbones.

Figure 2:
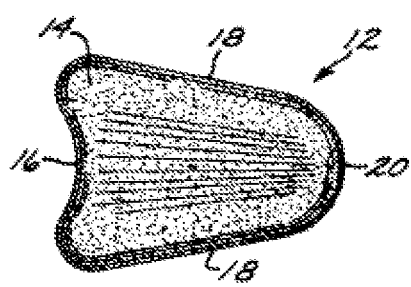
FIG. 2 is a bottom plan view of the device of FIG. 1.
Figure 4:
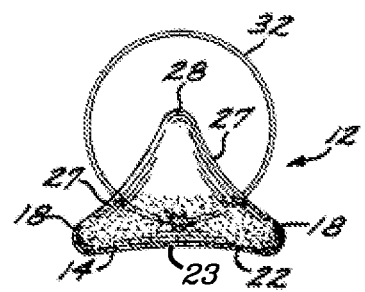
FIG. 4 is an anterior elevational view of the device of FIG. 1.
Figure 7:
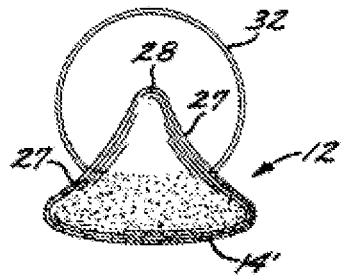
FIG. 7 is an anterior elevational view of a first modified form of the first embodiment.

The body 12 includes a base 14 that has the general outline of a blunt arrowhead, as shown in FIG. 2. In the first embodiment, the base 14 may be slightly concave, as shown in FIG. 4. Alternatively, the base 14 can be made slightly convex, as shown in FIG. 7, for those users who might find such a configuration more comfortable to wear. The base 14 may have a concave posterior end 16, as shown in FIG. 2, with lateral edges 18 that taper slightly toward each other as they extend toward a rounded anterior end 20. The anterior end 20 is thus somewhat narrower than the posterior end 16.

Figure 5:
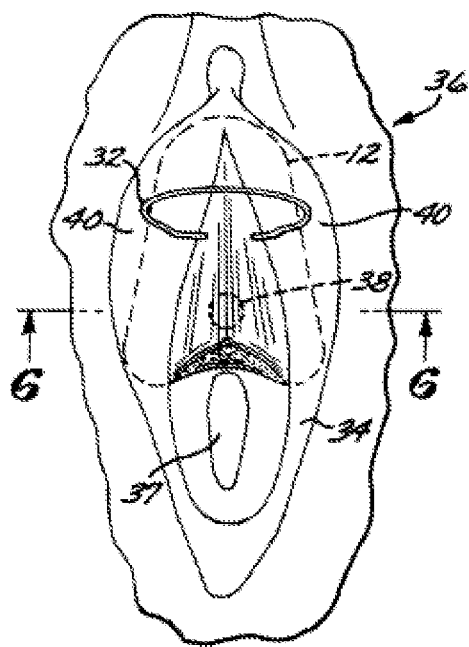
FIG. 5 is plan view of the device of FIG. 1, showing the device installed in the external genitalia of a human female.
Figure 6:
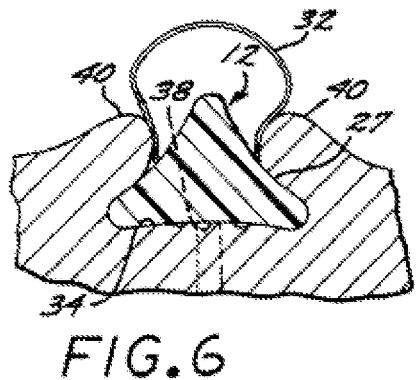
FIG. 6 is a cross-sectional view taken along line 6-6 of FIG. 5.

The body 12 is provided with an adhesive surface 23 for retention against the floor of the vestibule 34 of the vulva 36 as described in relation with FIGS. 5 and 6. In this embodiment, the base 14 is coated with an adhesive layer 22, comprising a pressure-sensitive, hydrophilic hydrogel adhesive material. Such hydrogel adhesives are marketed by R & D Medical Products, Lake Forest, Calif., under the trademark "PROMEON". The hydrogel composition may include from about 25 to about 50 weight percent polyvinyl pyrrolidone (PVP) or about 30 to about 40 weight percent. The polyvinyl pyrrolidone may have a weight average molecular weight in the range of about 100,000 to 600,000, or in the range of about 300,000 to 400,000. A suitable polyvinyl pyrrolidone is type NP-K90 commercially available from Irvine Scientific, Santa Ana, Calif.

The composition may also include polyvinyl alcohol in a weight percentage of about 2 to about 5 or about 3 to about 4 weight percent. A particular polyvinyl alcohol is sold by the E. I. DuPont de Nemours & Co. under the trade designation "Elvanol HV". Generally speaking, polyvinyl alcohol suitably may have a weight average molecular weight in the range of about 150,000 to about 300,000, or about 170,000 to about 220,000. A particular PVA is the material available from E. I. du Pont de Nemours & Co. having a stated molecular weight of about 185,000.

The polyvinyl alcohols may be generally at least about 75% hydrolyzed. PVA may be about 100% hydrolyzed.

The composition may also include about 5 to about 40 weight percent, or about 15 to about 25 weight percent polar plasticizer or humectant e.g., glycerol. Other useful polar plasticizers include propylene glycol, sorbitol, poly(ethylene)glycol, for example having a molecular weight in the range of about 200 to about 20,000, or polypropylene glycol, for example having a molecular weight in the range of about 500 to about 5,000. Other polar plasticizers or humectants will be well-known to one skilled in the hydrogel art.

The composition may also include the presence of about 3 to about 50 weight percent water in the resulting matrix. Deionized water is may be used. This percentage of water may provide suitable adhesiveness, tack, cohesive strength, and skin-compatibility.

One skilled in the art will recognize that it is possible to add small amounts of other materials to adjust the properties of the present composition for a particular end use. For example, if it is chosen to increase the tackiness of the gel, poly-2-acrylamido 2-methyl propane sulfonic acid poly (AMPS) (or its salts) may be employed. Other material which can be employed to increase tackiness include polyacrylic acid, polystyrene sulfonic acid or salts thereof, karaya, xanthan, guar or locust bean gums. Tackifiers above described may generally be present in the range of about 2 to about 20 weight percent.

For some applications, it may be chosen to increase the internal coherence, cohesiveness or strength of the present biomedical composition. In such instances, materials such as hydroxy propyl methyl cellulose, carboxy methyl cellulose, hydroxy propyl guar, dextran or silica may be added. One skilled in the art will recognize other materials which could be added to the composition described herein to adjust various desired properties. Generally speaking, such additives may be present in the range of about 0 to about 10 weight percent.

For preparation of the materials, generally speaking, a temperature-controlled, stirrable reactor may be employed. The a reactor may be preheated to about 90° C., set to mix at approximately 100 revolutions per minute, and the following materials (in representative quantities):

1. deionized $H_2O$—39 weight percent
2. glycerol polar plactizers (Mallinckrodt, Inc.)—22 weight percent
3. polyvinyl alcohol (duPont Elvanol HV)—4 weight percent
4. polyvinyl pyrrolidone (R & D Medical Products)—35 weight percent would be mixed, for example in the order indicated. The temperature of the closed mixer then would be increased to approximately 130° C. while maintaining stirring. After a temperature of approximately 130° C. is obtained, the temperature of the mixture would be decreased to approximately 95° C., the mixer subsequently turned off and the material poured onto a release paper (e.g., "Polyslick"), the gel thereby being cooled to a solid, non-liquid state.

Another type of adhesive that has shown good results is a mixture of poly 2-hydroxyethyl methacrylate (PHEMA) and polyethylene glycol (PEG) as a plasticizer. The percentage of PHEMA may range from about 45% to about 75%, with a corresponding range of PEG of about 55% to about 25%. A particular composition is about 53% to about 54% PHEMA and about 47% to about 46% PEG. Lower percentages of PHEMA yield greater adhesiveness, while higher percentages of PHEMA yield greater durability. The PEG may have a molecular weight between about 400 and about 1000. The PHEMA may be a mixture of low molecular weight PHEMA (molecular weight between about 10,000 and about 100,000) and high molecular weight PHEMA (molecular weight greater than about 100,000). The low molecular weight PHEMA provides adhesive properties, while the high molecular weight PHEMA improves adhesive structural integrity. The PHEMA mixture may be between about 10% to about 50% low molecular weight PHEMA and between about 90% and about 50% high molecular weight PHEMA, with the precise mixture being determined by the particular adhesive properties desired.

While a possible plasticizer is PEG, as described above, other plasticizers can be used, such as propylene glycol, polypropylene glycol (PPG), or glycerin.

If the body 12 is made of TDI or MDI, the material of the body 12 itself can be rendered adhesive by combining the TDI or MDI one-to-one by weight with about 0.25 to about 0.50 molar ammonium hydroxide during the water actuation of the foam. The resulting material has a surface that is positively charged, so that it will adhere to a negatively-charged mucoid surface (such as the surface of the vestibule 34 and the inner portions of the labia minora).

Alternatively, the entire body 12 can be formed of an adhesive, such as the PHEMA/PEG mixture described above. In many medical or body contact applications, a PHEMA is used which is made from an optical grade HEMA monomer. This optical grade HEMA monomer may, for example, have a purity of 99% and be expensive to produce and acquire. In the embodiments described within, PHEMA made from a HEMA monomer having a purity of between about 96% to about 98% can be used with good results.

Figure 1:
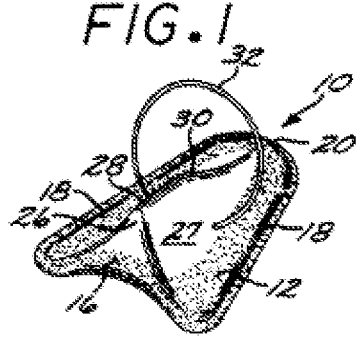
FIG. 1 is a perspective view of a female urinary incontinence device, in accordance with a first embodiment.
Figure 3:
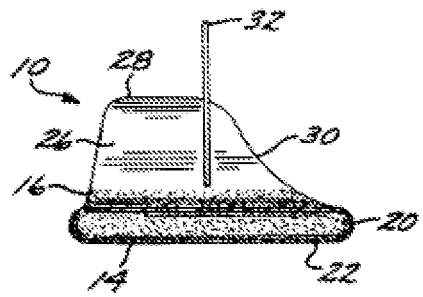
FIG. 3 is a side elevational view of the device of FIG. 1.

The side of the body 12 opposite the base 14 includes a central longitudinal stiffening ridge 26 which forms the thickest part of the body 12. If one adopts the convention that the base 14 is the "bottom" of the body 12, then the body 12 can be defined as having a surface 27 opposite the base that slopes "downwardly" from either side of the ridge 26 toward the edges 18, so that there is a gradual reduction in body 12 thickness from the ridge 26 to the edges 18. Viewed another way, the body 12 can be defined as having a cross-sectional shape that narrows from the base 14 to the "top" or apex 28 of the ridge 26. The resulting configuration is such that a lateral cross section of the body 12, taken through the ridge 26, produces a shape resembling a triangle with rounded corners and slightly concave sides, as shown in FIG. 6. Similarly, the ridge 26 has an anterior edge 30 that tapers "downwardly" from the apex 28 toward anterior end 20 of the body 12, as shown in FIG. 3, so that the anterior end 20 of the body 12 is substantially reduced in thickness as compared to the posterior end 16.

The female urinary incontinence device 10 may be provided with a handle or tab that is either integrally molded with the body 12, or subsequently attached to it. In the first embodiment, handle is a ring or loop 32, for example of thread, that is inserted laterally through the body 12. The loop may be located near the anterior portion of the apex 28 of the ridge 26, depending on the embodiment.

FIGS. 5 and 6 show the female urinary incontinence device 10 installed in the external genitalia of a human female. The female urinary incontinence device 10 is installed so that the base 14 is seated against the vestibule 34 of the vulva 36, anteriorly of the vaginal orifice 37, thereby occluding the urethral meatus 38. The adhesive surface 23, provided by the adhesive layer 22 on the base 14, is configured to seal the urethral meatus 38 to prevent the escape of urine. The lateral edges 18 and the anterior end 20 of the body 12 are tucked under the labia minora 40. The engagement between the labia minora 40 and the sloping surface 27 enhances the retention of the body 12 in engagement with the vestibule 34. The concavity in the posterior end 16 of the body 12 allows for somewhat greater surface area for engagement by the labia minora 40, while leaving a clearance for the vaginal opening 37. The ridge 26 extends into the interlabial space, and the loop 32 protrudes from between the labia majora (not shown), so as to be exposed to facilitate manual grasping, for removal of the female urinary continence device 10.

The body 12 can be provided in a number of sizes to fit a large variety of individuals. The length of the body 12 can be made to be approximately the same as the distance between the anterior lip of the vaginal orifice and the juncture of the labia minora 40. The width of the body 12 may be chosen to conform substantially to the width of the vestibule 34. Predetermined sizes can be trimmed individually for optimum fit. In some cases, a mold of the relevant portions of the vulva may be taken prior to sizing the pad.

The adhesive layer 22 not only provides a fluid-tight seal for the urethral meatus 38, but it also minimizes slippage of the female urinary incontinence device 10. The central ridge 26 lends rigidity that resists deformation of the body 12 and rupture of the adhesive layer 22 under fluid pressure from the urethra, thereby enhancing the fluid-tight seal provided by the body 12 against the urethral meatus 38. It may be chosen to extend the adhesive layer 22 onto the labia-engaging surface 27, thereby further enhancing the stability of the female urinary incontinence device 10.

A female urinary incontinence device 10 constructed in accordance with the first embodiment, as described above, can be made to withstand short-term fluid pressures from the urethra in the range of up to at least about 100, and preferably about 170, centimeters of water without significant leakage, as least for a short period of time. For example, for about two seconds or greater, and preferably about three seconds or greater. Pressures on this order are those that would typically result in involuntary urine voiding in cases of stress and urge incontinence. 170 centimeters of water is the approximate maximum bear-down pressure for a typical adult human female.

As an option, the foam material of the body 12, and/or the adhesive surface 23, can be provided with a medically-active composition. An antibacterial or germicidal agent, such as silver oxide or silver azide may be used, for example.

Figure 8:
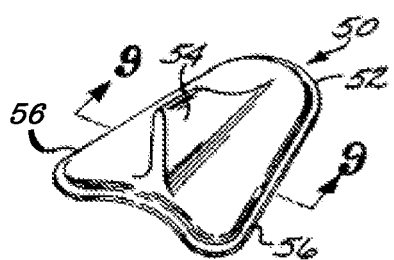
FIG. 8 is a perspective view of a second modified form of the first embodiment.
Figure 9:
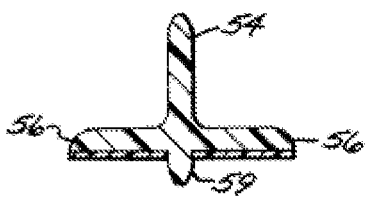
FIG. 9 is cross-sectional view taken along Line 9-9 of FIG. 8.
Figure 10:
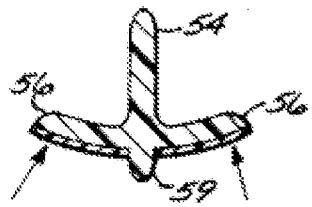
FIG. 10 is a cross-sectional view, similar to that of FIG. 9, showing the flexing of the lateral edges of the body of the female urinary incontinence device in accordance with the first embodiment.
Figure 11:
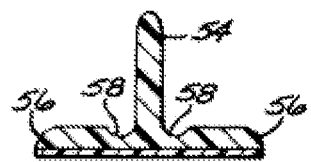
FIG. 11 is a cross-sectional view of a third modified form of the first embodiment.
Figure 12:
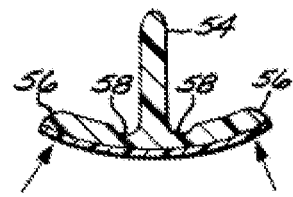
FIG. 12 is a cross-sectional view, similar to that of FIG. 11, showing the flexing of the lateral edges of the body.

The first embodiment lends itself to several modifications that may provide better comfort for certain individuals. For example. FIGS. 8, 9, and 10 show a modified device 50, which includes a body 52 of substantially uniform thickness, except for a longitudinal ridge 54. This modification provides lateral flaps 56 that flex more easily than those of the embodiment of FIGS. 1-7 when engaged against the labia minora 40, thereby yielding a better conformal fit with the genitalia. Still greater flexibility may be provided by forming a longitudinal groove 58 in each of the flaps 56, on either side of the ridge 54, as shown in FIGS. 11 and 12.

As still another option, a short protuberance 59 may be provided on the base 14, as shown in FIGS. 9 and 10. The protuberance 59 is dimensioned to be received wholly or partially within the urethral meatus 38, thereby facilitating proper placement of the female urinary incontinence device 10, and enhancing the occlusion of the urethral meatus 38.

Another modification of the first embodiment is shown in FIGS. 17, 18, and 19. As shown in these figures, a modified female urinary incontinence device 60 includes a layer 62 of highly-absorbant hydrophilic material adjacent the adhesive layer 64 on the base of the female urinary incontinence device 60. The hydrophilic layer 62 can be a mixture of the PHEMA/PEG adhesive and either a microsponge material, such as carboxymethylcellulose (CMC) or a super-absorbant material, such as potassium polyacrylate. The hydrophilic layer 62 draws moisture from the adhesive layer 64 and absorbs the moisture, thereby prolonging the useful lifetime of the adhesive by delaying saturation. Absorption of moisture causes the hydrophilic layer 62 to swell, as shown in FIG. 19, which may enhance the sealing properties of the female urinary incontinence device 60.

Still another modification of the first embodiment is shown in FIGS. 20, 21 and 22. In these figures, a modified female urinary incontinence device 70 has a body 72 having an integral longitudinal ridge 74. The ridge 74 a finger hole 76 in its posterior edge. The finger hole 76 may normally be in a collapsed state, as shown in FIG. 20. It may expand to receive the user's finger 78, as shown in FIG. 22, to facilitate installation and removal.

In FIG. 21, the female urinary incontinence device 70 is shown as having an adhesive layer 80 applied directly to the base of the body 72, as previously described. FIG. 23 shows still another feature that can be incorporated, as a further modification, into any of the previously-described variations of the first embodiment. In this variation or modification, a scrim layer 90 is enclosed within the adhesive 92 applied to the base of the body 72. The scrim layer 90 may be a thin, non-woven sheet of polyester that can reinforce an elastomeric material. In the present embodiment, the scrim layer 90 adds structural integrity to the adhesive material, thereby enhancing the durability of the female urinary incontinence device 70. As shown in FIG. 23, the scrim layer 90 is placed in the adhesive before the adhesive is cured to a semi-solid. Alternatively, the scrim layer 90 can be applied to the base of the body 72 before the adhesive is applied, in which case the scrim layer would be sandwiched between the adhesive and the base of the pad.

Figure 13:
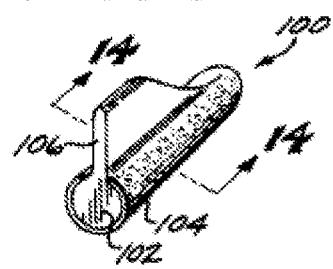
FIG. 13 is a perspective view of a second embodiment.
Figure 14:
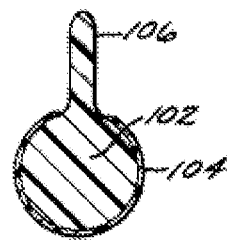
FIG. 14 is a cross-sectional view taken along Line 14-14 of FIG. 13.
Figure 15:
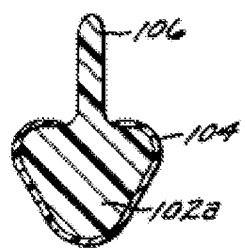
FIG. 15 is a cross-sectional view, similar to that of FIG. 14, showing a modified form of the second embodiment.
Figure 16:
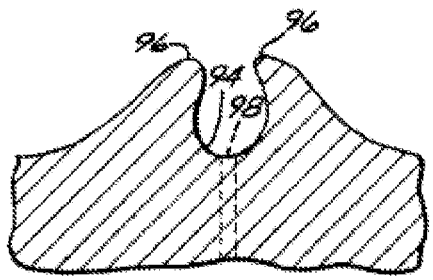
FIG. 16 is a cross-sectional view of the external female genitalia, showing a vestibule of the configuration for which the second embodiment is adapted.

It has been noted that some potential users of the embodiments disclosed have a relatively narrow vestibule floor. This type of anatomical structure is shown in FIG. 16, which shows a simplified cross-sectional view of external female genitalia, wherein the vestibule floor 94 and the labia minora 96 define a relatively narrow space proximate the urethral meatus 98. For those with this type of anatomical structure, the above-described first embodiment may be uncomfortable, or altogether unsuitable. Consequently, a second embodiment, illustrated in FIGS. 13, 14, and 15, is contemplated for such users.

In accordance with this second embodiment, a female urinary incontinence device 100 includes substantially tubular body 102, substantially the entire exterior surface of which is coated with an adhesive 104, of a type described above. The body 102 has a longitudinal ridge 106, for example, not coated with the adhesive, that is used as a gripping element to facilitate installation and removal. As shown in FIGS. 13 and 14, the body 102 may have a substantially elliptical cross-section. Alternatively, as shown in FIG. 15, a body 102a, having a cross-sectional shape similar to a rounded triangle, may be more suitable for some users. Optionally, a protuberance (not shown), such as the protuberance 59 shown in FIGS. 9 and 10 and described above, can be provided on this embodiment to facilitate proper placement and to enhance occlusion.

FIGS. 24 and 25 illustrate a third embodiment. A female urinary incontinence device 110, in accordance with this embodiment, includes a thin, flexible sac or bladder 112, formed of polyurethane or a similar thin, resilient, flexible material. The sac 112 is filled with a suitable biocompatible liquid or gel 114 by means of a needle, and the needle hole is then sealed, thereby forming a compliant sac. A possible material for filling the sac is a hydrogel, similar in some embodiments to the hydrogel adhesives described herein. Substantially the entire exterior surface of the sac is coated with an adhesive 116, of a type described above.

In use, the device 110 is inserted under the labia minora 40 so as to be seated against the floor of the vestibule 34, occluding the urethral meatus 38. The sac conforms to the anatomical structure of the external female genitalia, filling the interlabial space, and sealing against the urethral meatus 38 with the aid of the adhesive 116. Because the sac 112 is so compliant, it can be used for a wide variety of anatomical structures, providing high levels of comfort. The device may be provided with a raised tab 118, not coated with the adhesive 116, to be gripped by the user, to facilitate the installation and removal of the female urinary incontinence device 110.

Figure 26:
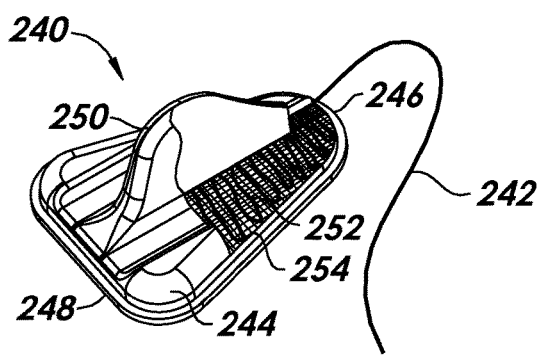
FIG. 26 is a perspective view of an embodiment of a female urinary incontinence device having a tether.

FIGS. 26 through 29 illustrate several embodiments of female urinary incontinence devices having a tether 242. In use, the tether 242 may be used to remove the female urinary incontinence devices. In some embodiments, the tether 242 may be used to manipulate the female urinary incontinence devices. FIG. 26 illustrates a female urinary incontinence device 240 comprising a body 244 having an anterior end 246 and a posterior end 248. A central longitudinal ridge 250 may be carried by the body 244 to aid with the placement of the female urinary incontinence devices 240. In some embodiments, the tether 242 may be molded into the body 244. In some embodiments, the tether 242 may have a back-and-forth, undulating pattern 252, so that it is well incorporated into the body 244, and will not pull out when a tensile force T (FIG. 27) is applied at the end of the tether 242. In some embodiments, a woven fabric 254 may be incorporated into the body 244 to add strength and to lessen the elongation of the body 244 towards the anterior end 246. The woven fabric 254 may reinforce the material of the body 244 and increase its overall tensile strength. In some embodiments, the woven fabric 254 may comprise a scrim. In some embodiments, the tether 242 may be incorporated into the woven fabric 254. In some embodiments, the tether 242 may be partially, substantially or completely woven into the woven fabric 242. In some embodiments, the undulating pattern 252 of the tether 242 may be interwoven into the woven fabric 254. In some embodiments, an adhesive layer 258 (FIG. 27) may be disposed upon a surface 256 of the body 244.

Figure 27:
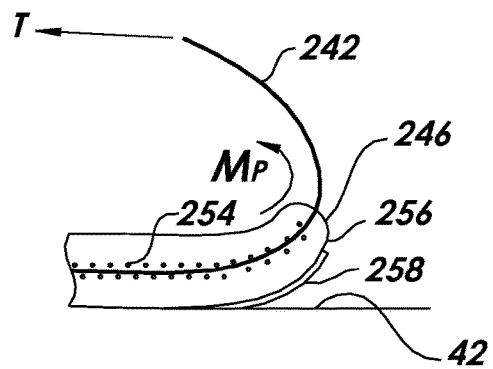
FIG. 27 is a cross-sectional view of an embodiment of the female urinary incontinence device having a tether of FIG. 26 being detached from the vestibule floor.
Figure 28:
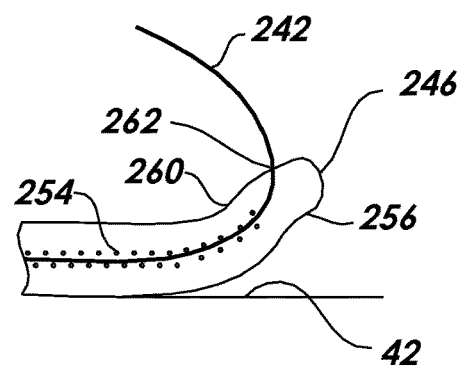
FIG. 28 is a cross-sectional view of an embodiment of a female urinary incontinence device.
Figure 29:
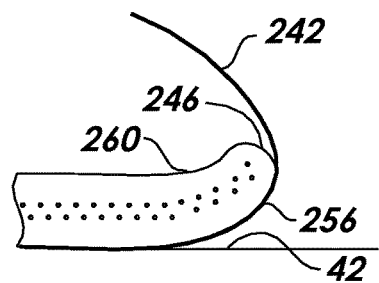
FIG. 29 is a cross-sectional view of an embodiment of a female urinary incontinence device.

In FIG. 27 the tensile force T applied on the tether 242 is applied in a direction generally towards the posterior end 248 of the female urinary incontinence device 240, which, because the tether 242 extends from the anterior end 246 of the female urinary incontinence device 240, cause a peeling moment $M_P$, which causes the adhesive layer 258 to detach (peel) from the vestibule floor 42. In the embodiment of FIG. 27, the tether 242 extends from the anterior end 246 of the body 244. In FIG. 28, the tether 242 extends from an upper portion 260 of the body 244. In some embodiments, as shown in FIG. 28, the tether extends from an upper portion 260 of the body 244, at a point 262 adjacent the anterior end 246 of the body 244. This allows the extending tether 242 to lie completely at the upper portion 260 of the body 244 while the female urinary incontinence device 240 is in place. In FIG. 29, an embodiment is illustrated wherein the tether 242 extends from the anterior end 246 of the body 244, adjacent the lower surface 256 of the body 244. This may lower the tensile stresses in the material of the body 244. In some embodiments, the tether 242 may be incorporated directly into the adhesive layer 258.

Figure 30:
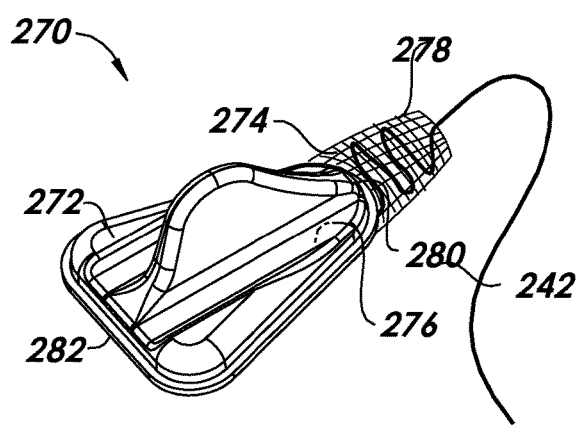
FIG. 30 is a perspective view of an embodiment of a female urinary incontinence device having a tether.

An embodiment of a female urinary incontinence device 270 having an anterior end 280 and a posterior end 282 is illustrated in FIG. 30 in which a woven fabric 274 is partially incorporated into the body 272. A proximal portion 276 of the woven fabric 274 is incorporated into the body 244, or the adhesive layer (not shown), and a distal portion 278 of the woven fabric 274 extends anteriorly from the anterior end 280 of the female urinary incontinence device 270. In some embodiments, the tether 242 may be woven into the woven fabric 274 at only the proximal portion 276 of the woven fabric, at only the distal portion 278 of the woven fabric 274, or at both the proximal portion 276 and the distal portion 278 of the woven fabric 274.

FIGS. 31 and 32 illustrate an embodiment of a female urinary incontinence device 1060 comprising a body 1062 having an anterior end 1064, a posterior end 1066, and having a central longitudinal ridge 1068 carried by the body 1062. As in any of the embodiments of the female urinary incontinence devices presented herein, the central longitudinal ridge 1068 may be replaced by any possible user interface, loop, tether, hole, tube, or other type of handle. In some embodiments, substantially the entire female urinary incontinence device 1060 from a first surface 1070 to a dorsal end 1072 is made from a silicone hydrogel. In some embodiments, the silicone hydrogel may comprise a water gradient silicone hydrogel, which, when hydrated, has a first water content at the first surface 1070 and a second water content at the dorsal end 1072. In some embodiments, the water gradient silicone hydrogel may have a first water content at the first surface 1070 and a second water content at the central longitudinal ridge 1068. In some embodiments, the first water content may be significantly less than the second water content. For example, the first water content may be lower than the second water content so that the first surface 1070 is tacky and can engage the vestibule floor 34 and/or occlude the urethral meatus 38, while one or more of the the upper surface 1061 of the body 1062, the central longitudinal ridge 1068, and/or the dorsal end 1072 may be lubricious, to aid in comfort. For example, the lubricious upper surface of the body 1062 or the lubricious central longitudinal ridge 1068 may allow portions of the anatomy like the labia majora to slide past and not be chafed or irritated. In some embodiments, the first surface 1070 may be tacky enough to act as the adhesive.

A silicone hydrogel that is capable, when hydrated, of having a water content of 50%, is said to have a 50% water holding capacity. In some embodiments, a first water holding capacity at the first surface 1070 may be less than a second water holding capacity at the central longitudinal ridge 1068 and/or the dorsal end 1072. In some embodiments, this difference is greater than about 10%. In some embodiments, this difference is greater than about 20%. In some embodiments, this difference is greater than about 30%. In some embodiments, this difference is greater than about 40%. In some embodiments, this difference is greater than about 50%. In some embodiments, the range between the first water holding capacity and the second water holding capacity may be between about 30% and about 80%. In some embodiments, the range between the first water holding capacity and the second water holding capacity may be between about 40% and about 70%. In some embodiments, the range between the first water holding capacity and the second water holding capacity may be between about 50% and about 60%. In some embodiments, an internal substrate 1074 may be located between the first surface 1070 and the central longitudinal ridge 1068 and/or the majority of the body 1062. In some embodiments, the silicone hydrogel is cross-linked with ultra-violet (UV) light. In some embodiments, the silicone hydrogel is at least partially masked during the cross-linking with the UV light. In some embodiments, the UV beam is attenuated during the cross-linking with the UV light.

Silicone hydrogels and methods for forming devices from silicone hydrogels may be used in certain embodiments, such as those described in U.S. publication No. 2012/0026458, filed Jul. 29, 2011, and entitled "Silicone Hydrogel Lenses with Water-Rich Surfaces," which is hereby incorporated by reference in its entirety for all purposes. Silicone hydrogels and methods for forming devices from silicone hydrogels may be used in certain embodiments, such as those described in U.S. publication No. 2015/0094393, filed Sep. 23, 2014, and entitled "Method for Making UV-Absorbing Ophthalmic Lenses," which is hereby incorporated by reference in its entirety for all purposes. In some embodiments, a wetting agent may additionally be used, in order to aid the wetting of the silicone hydrogel. In some embodiments, the wetting agent may be an internal wetting agent (within the female urinary incontinence device 1060). In some embodiments, the wetting agent may comprise hyaluronic acid, methacrylated hyaluronic acid, or poly (oxyethylene)-poly(oxybutylene). In some embodiments, the wetting agent may be photocrosslinkable.

In some embodiments, the manufacturing process of the female urinary incontinence device 1060 may be done using reusable molds. In some embodiments, the reusable molds may comprise silica glass. In some embodiments, the reusable molds may comprise quartz. In some embodiments, the reusable molds may comprise a water-soluble polymer. Materials and methods for forming devices may be used in certain embodiments, such as those described in U.S. Pat. No. 5,508,317, filed Aug. 4, 1994, and entitled, "Photocrosslinked Polymers," which is hereby incorporated by reference in its entirety for all purposes. Materials and methods for forming devices may be used in certain embodiments, such as those described in U.S. Pat. No. 6,800,225, filed Jul. 14, 1994, and entitled, "Process and Device for the Manufacture of Mouldings and Mouldings Manufactured in Accordance with that Process," which is hereby incorporated by reference in its entirety for all purposes. Materials and methods for forming devices may be used in certain embodiments, such as those described in U.S. Pat. No. 8,163,206, filed Jun. 16, 2009, and entitled, "Method for Making Silicone Hydrogel Contact Lenses," which is hereby incorporated by reference in its entirety for all purposes.

FIGS. 33 and 34 illustrate another embodiment of a female urinary incontinence device 1100 comprising a silicone hydrogel, such as a water gradient silicone hydrogel. The female urinary incontinence device 1100 comprises a body 1102 having an anterior end 1104, a posterior end 1106, and a tether 1108. The tether 1108 has a first end 1110 and a second end 1112, the first end 1110 of the tether 1108 incorporated into the body 1102 and the second end 1112 configured for grasping, such that a tensile force can be placed on at least a portion of the body to aid its removal from between the labia minora and the vestibule floor. In some embodiments, substantially the entire female urinary incontinence device 1100 from a first surface 1116 to a dorsal end 1118 is made from a water gradient silicone hydrogel. In some embodiments, the water gradient silicone hydrogel is configured such that the first (bottom) surface 1116 has a tacky or sticky characteristic, while the remaining surface 1120 of the body 1102 is not significantly tacky or sticky.

FIGS. 35 and 36 illustrate another embodiment of a female urinary incontinence device 1130 comprising a silicone hydrogel, such as a water gradient silicone hydrogel. The female urinary incontinence device 1130 comprises a body 1132 having an anterior end 1134, a posterior end 1136, and a tether 1142. The tether 1142 may be similar to the tether 1108 previously described. In some embodiments, substantially the entire female urinary incontinence device 1130 from a first surface 1144 to a dorsal end 1146 is made from a water gradient silicone hydrogel. In some embodiments, the water gradient silicone hydrogel is configured such that the a first three-dimensional surface 1140 has a tacky or sticky characteristic, while a second three dimensional surface 1138 is not significantly tacky or sticky. The first three-dimensional surface 1140 is depicted in FIGS. 35 and 36 with an "x" pattern, while the second three dimensional surface 1138 is not. The first three-dimensional surface 1140 may also be described as an adhesive surface a second three dimensional surface 1138 may also be described as a non-adhesive surface. The location of the adhesive and non-adhesive surfaces may be controlled by one or more processes. For example, cornstarch may be controllably applied (e.g., by masks or templates) to the second three-dimensional surface 1138 in order to reduce its tackiness. Other surface treatments may be applied to one or both of the first three-dimensional surface 1140 and/or second three dimensional surface 1138, including but not limited to corona discharge, plasma discharge, cleaning, degreasing, chemical etching, acid etching, mechanical etching, photoetching, application of surface additives, primer application, solvent application, mechanical abrasion, or blasting with particles, including silica-based particles. Any of these processes may be used to alter or control the water holding capacity of first three-dimensional surface 1140 and/or second three dimensional surface 1138.

The resulting female urinary incontinence devices 1130, 1060, 1100 as described, by their improved physical properties may have increased breathability, allowing for improved comfort to the wearer and better skin hydration and moisture control. In addition the wearer may experience better odor control, as the skin demonstrates improved moisture balance. Comfort for the wearer is also increased because of better temperature control. Additionally, if a medicant is infused, absorption of the medicant can be increased and/or optimized.

From the foregoing, the features of the present invention will be readily appreciated. The incontinence device in accordance with the present invention provides effective management of female urinary incontinence, such as stress incontinence, without the inconvenience and discomfort associated with prior art urine collection devices and absorbent pads. The present invention is easy to use and comfortable to wear. It is easily shaped and sized to fit each individual user's anatomy with optimum effectiveness and comfort. Easily and inexpensively manufactured, the present invention can be made as a disposable item.

While embodiments have been shown and described, various modifications may be made without departing from the scope of the inventive concepts disclosed herein.

What is claimed is:

1. A system for managing female incontinence comprising:
    a body of biocompatible material configured to fit between the labia minora and the vestibule floor, the body having a surface configured to occlude the urethral meatus;
    an adhesive carried on at least a first portion of the surface and configured to provide a sealing engagement between the body and the urethral meatus; and
    wherein at least the adhesive comprises a water gradient silicone hydrogel.

2. The system of claim 1, wherein the water gradient silicone hydrogel has a plurality of regions having different water holding capacities, and wherein the water gradient silicone hydrogel has a range between the lowest water holding capacity and highest water holding capacity of between about 30% and about 80%.

3. The system of claim 2, wherein the water gradient silicone hydrogel has a range between the lowest water holding capacity and highest water holding capacity of between about 40% and about 70%.

4. The system of claim 2, wherein the water gradient silicone hydrogel has a range between the lowest water holding capacity and highest water holding capacity of between about 50% and about 60%.

5. The system of claim 1, wherein the water gradient silicone hydrogel has a plurality of regions having different water holding capacities, and wherein a difference between the lowest water holding capacity and highest water holding capacity is greater than about 10%.

6. The system of claim 5, wherein the difference between the lowest water holding capacity and highest water holding capacity is greater than about 20%.

7. The system of claim 5, wherein the difference between the lowest water holding capacity and highest water holding capacity is greater than about 30%.

8. The system of claim 5, wherein the difference between the lowest water holding capacity and highest water holding capacity is greater than about 40%.

9. The system of claim 5, wherein the difference between the lowest water holding capacity and highest water holding capacity is greater than about 50%.

10. The system of claim 1, wherein the adhesive and the body each comprise a water gradient silicone hydrogel.

11. The system of claim 10, wherein the adhesive has a first water holding capacity and the body has a second water holding capacity, and wherein the first water holding capacity is less than the second water holding capacity.

12. The system of claim 11, wherein a difference between the lowest water holding capacity and highest water holding capacity is greater than about 10%.

13. The system of claim 11, wherein the difference between the lowest water holding capacity and highest water holding capacity is greater than about 20%.

14. The system of claim 11, wherein the difference between the lowest water holding capacity and highest water holding capacity is greater than about 30%.

15. The system of claim 11, wherein the difference between the lowest water holding capacity and highest water holding capacity is greater than about 40%.

16. The system of claim 11, wherein the difference between the lowest water holding capacity and highest water holding capacity is greater than about 50%.

17. The system of claim 10, further comprising an internal substrate between the adhesive and the body.

18. The system of claim 17, wherein the water gradient silicone hydrogel is cross-linked with UV light.

19. The system of claim 10, wherein the adhesive and body each consist of a water gradient silicone hydrogel.

20. The system of claim 10, wherein the water gradient silicone hydrogel is cross-linked with UV light.

21. The system of claim 1, wherein the water gradient silicone hydrogel comprises a photocrosslinked polymer.

22. The system of claim 10, wherein the water gradient silicone hydrogel comprises a photocrosslinked polymer.

23. The system of claim 1, further comprising a wetting agent.

24. The system of claim 23, wherein the wetting agent is an internal wetting agent.

25. The system of claim 24, wherein the internal wetting agent comprises hyaluronic acid.

26. The system of claim 25, wherein the internal wetting agent comprises methacrylated hyaluronic acid.

27. The system of claim 23, wherein the wetting agent comprises poly(oxyethylene)-poly(oxybutylene).

28. The system of claim 23, wherein the wetting agent is photocrosslinkable.

29. The system of claim 1, wherein the body comprises a molded structure.

30. The system of claim 1, wherein the body and the adhesive comprise a molded structure.

* * * * *